United States Patent [19]

Tang et al.

[11] Patent Number: 4,488,953

[45] Date of Patent: Dec. 18, 1984

[54] PURIFICATION OF RECYCLED PARAFFINS IN PHOTOCHLORINATION PROCESS

[75] Inventors: David Y. Tang, Tonawanda; James G. Colson, Williamsville, both of N.Y.

[73] Assignee: Occidental Chemical Corporation, Niagara Falls, N.Y.

[21] Appl. No.: 504,005

[22] Filed: Jun. 13, 1983

[51] Int. Cl.³ .................... C07C 17/00; C07C 26/00
[52] U.S. Cl. ............................................. 204/163 R
[58] Field of Search ..................... 204/163 R, 158 HA

[56] References Cited

U.S. PATENT DOCUMENTS

| | | | |
|---|---|---|---|
| 2,492,941 | 12/1949 | Sconce et al. | 204/163 R |
| 2,915,428 | 12/1959 | Weinberg et al. | 204/163 R |
| 3,378,476 | 4/1968 | Hutson et al. | 204/163 R |
| 3,418,388 | 12/1968 | Hurley et al. | 260/671 |
| 3,567,610 | 3/1971 | Krol et al. | 204/163 R |
| 3,639,494 | 2/1972 | Crocker | 204/163 R |
| 3,654,107 | 4/1972 | Lindwall et al. | 204/163 R |
| 3,911,004 | 10/1975 | Hertel et al. | 204/163 R |
| 4,013,729 | 3/1977 | Suggitt et al. | 260/632 C |
| 4,042,490 | 8/1977 | Suggitt et al. | 208/264 |
| 4,242,187 | 12/1980 | Schlacht et al. | 204/163 R |
| 4,300,005 | 11/1981 | Li | 570/244 |

FOREIGN PATENT DOCUMENTS 2805441  8/1979  Fed. Rep. of Germany .

OTHER PUBLICATIONS

Wang, B. et al., Chemical Abstracts, vol. 96 (21), Abstract 180705x, (Kexue Tonghad, vol. 27(3), 191, (1982)), (1982).
Gouverneur, P. et al., Chemical Abstracts, vol. 72 (20), Abstract 105, 825n, (Bull. Cl. Sci. Acad. Roy. Belg. (1969)), (1970).
Yaminov, M. S. et al., Chemical Abstracts, vol. 75 (13), Abstract 87930y, (Zh. Prikl. Khim. (1971), vol. 4, p. 1381), 1971.
Sergeev, G. B. et al., Chemical Abstracts, vol. 100 (2), Abstract 15211b, (Kinet. Katal (1983), vol. 24 (5), 1046), 1984.
Kelly, C. C. et al., Can. J. Chem., (1970), vol. 48 (4), pp. 603–606.

*Primary Examiner*—Leland A. Sebastian
*Assistant Examiner*—M. Moskowitz
*Attorney, Agent, or Firm*—James F. Tao

[57] ABSTRACT

An improved process for the photochlorination of normal paraffins to prepare mono-chlorinated alkanes, in which the normal paraffin feed stream is only partially chlorinated and the unreacted normal paraffins separated and recycled, the recycled unreacted paraffin being treated with a basic material capable of removing polar impurities therefrom which may hinder the photochlorination reaction.

9 Claims, No Drawings

PURIFICATION OF RECYCLED PARAFFINS IN PHOTOCHLORINATION PROCESS

BACKGROUND OF THE INVENTION AND PRIOR ART STATEMENT

This invention relates to a process for mono-chlorinating paraffins. More particularly, the invention pertains to a process for the purification of recycled paraffins in a mono-chlorination process.

The photochlorination of paraffins to form alkyl chlorides is well known in the art. Thus, Sconce et al. U.S. Pat. No. 2,492,941 discloses a process for the complete chlorination of hydrocarbons by first treating a partially chlorinated hydrocarbon, such as chloropropane, with alkali metal and alkaline earth hydroxides or alkali metal carbonates, and then chlorinating the treated material to obtain ochtachloropropane. Stretton et al. U.S. Pat. No. 2,916,428 discloses a process for making a chlorinated wax product having a high chlorine content and other desired properties by chlorinating a waxoil feed mixture containing a major proportion of a soft paraffin wax and minor proportion of a hydrocarbon oil. The chlorinated wax product of Stretton et al. is said to be useful in the preparation of mastic floor and wall tiles. In Hurley et al. U.S. Pat. No. 3,418,388 there is disclosed a process for chlorinating normal paraffins and then alkylating benzene with the resultant alkyl chlorides to produce an alkly benzene mixture, which may be used to produce a detergent by sulfonation. The process of Hurly et al. favors the formation of secondary normal alkyl chlorides by conducting the photochlorination reaction while the normal paraffins are dissolved in benzene. Contrary to the Hurley et al. disclosure, McCoy U.S. Pat. No. 3,948,741 discloses a chlorination process favoring the formation of terminally substituted alkanes, which are said to be valuable chemical intermediates in the production of fatty acids, amines, and sulfonates for use as detergents, etc. The method of McCoy consists of chlorinating a mixture of a normal paraffin hydrocarbon and a diluent-solvent of a chlorinated or fluorinated aliphatic hydrocarbon.

As indicated in the Hurley et al. patent, normal alkyl mono-chlorides are useful in the alkylation of benzene with subsequent sulfonation to produce a detergent, while alkyl polychlorides will react with the benzene to form undesirable diphenyl alkanes. To favor the production of alkyl mono-chlorides while suppressing the formation of alkyl polychlorides, the photochlorination reaction is normally conducted at a rate such that only about 20 to 30 mole percent of the normal paraffins starting material has been chlorinated. This procedure results in a large amount of unreacted normal paraffins which must be recycled to the photochlorination reactor to make the process commercially feasible. It has been found that when such large amounts of the unreacted normal paraffins are to be recycled and combined with fresh normal paraffins for feeding to the photochlorination reactor, the photochlorination reaction is sometimes retarded and the entire process upset.

It is, accordingly, an object of the present invention to provide an improved process for the photochlorination of normal paraffins in which the recycling of a large proportion of the paraffins would not retard the photochlorination reaction. It is another object of the invention to provide an improved photochlorination process in which certain undesirable impurities are removed from unreacted paraffins before they are recycled to the photochlorination reactor. These and other objects of the invention will become apparent from the following description.

SUMMARY OF THE INVENTION

We have now found that the deleterious effects of recycling large proportions of unreacted paraffins in the mono-chlorination of normal paraffins can be obviated by treating the unreacted normal paraffins with a basic material capable of removing certain polar compounds which may be present in the unreacted normal paraffins. The preferred basic materials for the removal of such polar compounds include certain alkali metal and alkaline-earth metal oxides.

DETAILED DESCRIPTION OF THE INVENTION

The present invention is concerned with the mono-photochlorination of normal paraffins to produce normal alkyl mono-chlorides, which may be used in an alkylation of benzene to produce an alkyl benzene mixture suitable for the manufacture of detergents. To produce such normal alkyl mono-chlorides, and to prevent the formation of undesirable normal alkyl polychlorides, the chlorination reaction is unually conducted to convert only about 20 to about 30 mole percent of the normal paraffins fed to the photochlorination reactor. This results in a large amount of unreacted normal paraffins which must be recycled. Generally, such unreacted normal paraffins can be conveniently separated from the alkyl mono-chlorides only after the alkylation reaction with benzene. It has been found that when such recycled unreacted normal paraffins are so separated and recycled, they sometimes retard or hinder the photochlorination reaction, which may be manifested in the much longer times required to reach a given degree of chlorination.

We have now found that the deleterious effects of such recycled unreacted normal paraffins can be eliminated by treating such unreacted normal paraffins with a basic material capable of removing polar compounds therefrom. It is believed that such polar compounds include phenol, substituted phenols, and certain amines. It is further believed that such polar compounds may be formed in the paraffinic stream during the photochlorination reaction or during or after the alkylation reaction with benzene.

Suitable normal paraffins or alkanes for use in the process of the invention generally have from about 6 to about 20 carbon atoms in the molecule. Preferably, the normal paraffins have from about 10 to 16 carbon atoms, and more preferably, the normal paraffins contain from about 10 to 14 carbon atoms. Such normal paraffins are commercially available and can be obtained, for example, by known treatments of kerosene.

The photochlorination reaction suitable for the process of the present invention is well known. Generally, it is preferable to conduct the photochlorination reaction by contacting gaseous chlorine with the normal paraffins in liquid form. The reaction is initiated by the use of suitable actinic light. The reaction temperature is an important variable in the photochlorination reaction. It is preferred to keep the initial temperature of the reacting gaseous and liquid mixture as low as possible, for example, at or somewhat below room temperature, such as 15° C. The chlorination reaction is exothermic and higher reaction temperatures tend to favor the formation of undesirable by-products. However, higher temperatures, such as 18°–78° C., may be used, particularly in conjunction with fast rates of throughput of the reacting materials. The reaction temperature may be maintained at a predetermined constant level throughout the photochlorination reaction, or the reacting mixture may be initially at a low temperature and permitted to gradually rise during the course of the reaction.

As indicated above, in order to favor the formation of normal alkyl mono-chlorides, and to substantially prevent the formation of alkyl polychlorides, the photochlorination reaction is generally conducted at a rate so that only about 20 to 30 mole percent of normal paraffins fed to the reactor has been chlorinated. Preferably, the mixture of gaseous chlorine and liquid paraffins is passed through the photochlorination reactor at a rate so that only about 25 mole percent of the paraffins have been chlorinated.

The partially chlorinated paraffin stream is generally used in an alkylation reaction with benzene before the unreacted paraffins are separated therefrom. The alkylation of benzene is generally conducted in the presence of aluminum chloride catalyst or other known catalysts.

After the alklation reaction, and after chlorine, benzene and the alkyl benzene mixture have been separated therefrom, the unreacted normal paraffins are then generally recycled to the photochlorination reactor. The recycled unreacted normal paraffins are generally combined with fresh make-up paraffins and the mixture contacted with chlorine in the photochlorination reactor. The presence of water in the paraffin stream may interfere with the photochlorination reaction and thus water, which may be introduced into the recycled unreacted normal paraffin stream, is removed prior to recycling into the photochlorination reactor.

In accordance with the process of the present invention, the unreacted normal paraffins are treated with a basic material capable of removing polar compounds therefrom prior to recycling into the photochlorination reactor. It is believed that such polar compounds include one or more of: phenol, substituted phenols and certain amines. Such polar compounds have an inhibiting effect on the photochlorination reaction between the normal paraffins and chlorine. Even relatively small amounts of phenol would inhibit the photochlorination reaction.

Suitable basic materials for use in the process of the present invention, which are capable of removing the objectionable polar compounds, include certain alkali metal and alkaline earth metal oxides. Examples of such suitable basic materials include magnesium oxide, aluminum oxide, calcium oxide, sodium oxide, and potassium oxide, etc. Although we do not wish to be bound by any explanation, it is believed that such basic materials accomplish the removal of the polar compounds by a combination of two factors: the phenol being slightly acidic, the basic materials chemically react with the phenol; and the polar compounds may be adsorbed on finely divided particles of the basic materials.

The contact between the unreacted normal paraffins and the basic material may be carried out in various known methods for contacting liquids with solids. We prefer to use the basic material in a solid bed filter and pass the unreacted normal paraffin stream therethrough in a continuous manner. Other known methods for such contacting may be used.

The basic materials suitable for the process of the present invention are preferably employed in a finely divided solid form. The solid form is much preferred and is almost a necessity in any commercial application of the process of the invention. Finely divided particulate solid basic material would provide a large surface area for contacting the liquid unreacted paraffins. In a continuous process for treating the unreacted paraffins, the finely divided solid basic material may be in the form of a bed in a filter through which the unreacted paraffins may be passed. In a batch type of treatment process, the finely divided solid basic material may be mixed with the liquid unreacted paraffins, and the mixture subsequently filtered to remove any remaining solids.

Basic materials other than the alkali metal and the alkaline earth metal oxides mentioned above may be effective in removing the polar compounds, such as phenol, but they are not preferred. For example, sodium hydroxide and potassium hydroxide will react with the slightly acidic phenol, but their use would be uneconmical in a commercial process. Sodium hydroxide might be used as an aqueous caustic solution which can be mixed with the unreacted paraffins, but any remaining moisture or caustic in the paraffin stream must be carefully and substantially completely removed since their presence would interfere with the chlorination reaction in the photochlorination reactor. This would generally necessitate the repeated washing and drying of the recycled paraffins. If the sodium hydroxide is to be used in a solid form, it is generally not possible to have a finely divided particulate solid, and relatively large particles of sodium hydroxide would present relatively small surface area for contact with the result that much of the treating material would be essentially wasted.

The invention will be further described with reference to the following examples.

EXAMPLE 1

A large three-neck glass flask was equipped with a magnetic stirring device. This flask was purged with argon. One neck of the flask was equipped with a dry ice-acetone condenser for condensing any chlorine which may have escaped from the reacting mixture in the flask. Another neck of the flask was equipped with a thermocouple which was connected to a recording device for recording the temperature of the materials in the flask with change in time. 125 Grams of fresh paraffin, consisting essentially of paraffins having 10 to 12 carbon atoms in each molecule, was charged into the flask, cooled to about $-20°$ to $-25°$ C. and maintained in the dark. About 13.5 grams of gaseous chlorine was introduced into the flask through a sparger in the third neck of the flask. The chlorine-paraffin mixture was allowed to warm to about 15° C. and then stirred vigorously after the light for the photochlorination reaction was turned on. The light source was 15-watt Sylvania Black Light Blue positioned about 36 inches from the flask. The exothermic photochlorination reaction was observed by the relatively rapid rise in temperature in the mixture in the flask. The temperature of the reacting mixture rose rapidly to a maximum point, after which time the temperature briefly stabilized and then slowly declined to approach that of the ambient temperature. The maximum temperature reached was 52° C. in 1.9 minutes from the starting point of the reaction period.

EXAMPLE 2

Recycled unreacted paraffin was obtained from a commercial plant in which paraffins containing 10 to 12 carbon atoms were photochlorinated and then reacted with benzene in an alkylation reaction. The unreacted paraffins were separated from the alkylated stream and used as the recycled unreacted paraffin in the examples herein. 127 Grams of such recycled paraffin was reacted with 13.7 grams of chlorine in accordance the procedure of Example 1. The maximum temperature of the reacting mixture reached was 48° C. in about 5.8 minutes after the initiation of the reaction.

EXAMPLE 3

The recyled and unreacted paraffin of Example 2 was treated with magnesium oxide in accordance with the following procedure. 127 Grams of recycled and unreacted paraffins was intimately mixed with about 10 grams of finely divided maglite (MgO) for about 30 minutes. The mixture was then filtered, and the filtrate was used as the treated recycled unreacted paraffins for photochlorination.

EXAMPLE 4

127 Grams of the treated recycled unreacted paraffins obtained in accordance with the procedure of Example 3 was photochlorinated in accordance with the procedure of Example 1. The chlorine added was 13.6 grams. The maximum temperature reached was 50° C. at about 1.4 minutes after the initiation of the photochlorination reaction.

EXAMPLE 5

The recycled unreacted paraffins obtained as in Example 2 above was treated with aluminum oxide in accordance with the following procedure. 100 Grams of the recycled unreacted paraffins were treated with about 10 grams of finely divided aluminum oxide by mixing the solid aluminum oxide with the liquid paraffins. After intimate mixing and allowing for adequate treatment times, the mixture was filtered and the filtrate used as the treated recycled unreacted paraffins.

EXAMPLE 6

The treated unreacted recycled paraffins obtained in accordance with the procedure of Example 5 was photochlorinated in accordance with the procedure of Example 1. 100 Grams of the unreacted recycled paraffins were mixed with 11 grams of chlorine. The maximum temperature reached was 50° C. at about 1.3 minutes after the initiation of photochlorination reaction.

From the foregoing descriptions and examples, it can be seen that recycled paraffins treated in accordance with the procedure of the present invention behaved substantially similarly to fresh paraffins. As compared to untreated recycled paraffins, the treated paraffins of the invention reached somewhat higher final reaction temperatures and consumed a reaction time which is less then one-fourth of that of the untreated recycled paraffins.

The invention has been described with reference to specific and preferred embodiments thereof, it will be appreciated by those skilled in the art that modifications and variations can be made without departing from the spirit and scope of the invention.

What is claimed is:

1. A process for the mono-chlorination of alkanes which comprises contacting normal alkanes containing from about 6 to about 20 carbon atoms with gaseous chlorine in a photochlorination reactor, said photochlorination step being conducted at a rate to substantially prevent the formation of alkyl polychlorides, passing the product stream from said photochlorination reactor into contact with benzene, separating unreacted normal alkanes from said product stream, passing said unreacted normal alkanes into contact with a basic material capable of removing polar impurities therefrom, and recycling the thus purified unreacted normal alkanes to said photochlorination reactor.

2. A process according to claim 1 wherein said basic material is selected from magnesium oxide, aluminum oxide, calcium oxide, sodium oxide, and potassium oxide.

3. A process according to claim 2 wherein said normal alkanes contain from about 10 to about 14 carbon atoms.

4. A process according to claim 3 wherein said photochlorination step is carried out at a speed to convert about 20 to 30 percent of said normal alkanes to normal alkyl monochlorides.

5. A process according to claim 3 further comprising substantially removing the water contained in said unreacted normal alkanes prior to contacting with said basic material.

6. A process according to claim 3 wherein said basic material is aluminum oxide.

7. A process according to claim 3 wherein said basic material is magnesium oxide.

8. A process according to claim 3 wherein said basic material is calcium oxide.

9. A process according to claim 1 wherein normal alkanes containing from about 10 to about 14 carbon atoms are contacted with gaseous chlorine in photochlorination reactor, and wherein said polar impurities are removed from said unreacted normal alkanes by contacting with aluminum oxide.

* * * * *